US008257681B2

(12) United States Patent
Stevenson et al.

(10) Patent No.: US 8,257,681 B2
(45) Date of Patent: Sep. 4, 2012

(54) COMPOSITIONS OF HIGH SPECIFIC ACTIVITY SN-117M AND METHODS OF PREPARING THE SAME

(75) Inventors: Nigel Raymond Stevenson, Sugar Hill, GA (US); Ian Martin Horn, Keller, TX (US)

(73) Assignee: Clear Vascular Inc., New York, NY (US)

( * ) Notice: Subject to any disclaimer, the term of this patent is extended or adjusted under 35 U.S.C. 154(b) by 681 days.

(21) Appl. No.: 12/344,340

(22) Filed: Dec. 26, 2008

(65) Prior Publication Data

US 2010/0166653 A1 Jul. 1, 2010

(51) Int. Cl.
*A61K 51/00* (2006.01)
*A61M 36/14* (2006.01)

(52) U.S. Cl. ........................ 424/1.61; 424/1.11; 424/9.1

(58) Field of Classification Search ........................ None
See application file for complete search history.

(56) References Cited

U.S. PATENT DOCUMENTS

| | | | |
|---|---|---|---|
| 5,280,505 A | 1/1994 | Hughey et al. |
| 5,409,677 A | 4/1995 | Zinn |
| 5,468,355 A | 11/1995 | Shefer et al. |
| 5,770,030 A | 6/1998 | Hamacher |
| 6,011,825 A | 1/2000 | Welch et al. |
| 6,231,832 B1 | 5/2001 | Srivastava |
| 6,503,477 B1 | 1/2003 | Srivastava |
| 6,541,514 B2 | 4/2003 | Srivastava et al. |
| 6,716,353 B1 | 4/2004 | Mirzadeh et al. |
| 6,751,280 B2 | 6/2004 | Mirzadeh et al. |
| 6,804,319 B1 | 10/2004 | Mirzadeh et al. |
| 6,917,044 B2 | 7/2005 | Amini |
| 2007/0071676 A1 | 3/2007 | Gonzales et al. |
| 2007/0140961 A1 | 6/2007 | Adelman |

FOREIGN PATENT DOCUMENTS

IL 84830 A * 1/1995

OTHER PUBLICATIONS

Dmitriev et al. Atomnaya Energiya, 1975, 135-137.*
Lieser. Nuclear and Radiochemistry, 2001, 32-35.*
Yano et al. Int, J. Appl. Rad. Isotop. 1973, 24, 319-325.*
Fukushima, et al., "The Production of High Specific Activities of Tin" Bulletin of the Chemical Society of Japan, vol. 36, No. 10 (1963) pp. 1225-1228.
Jansen, "Developing a Method for the Production of High Specific Activity 117m Sn from Tin Oxides Using the Szilard-Chalmers Effect", Proceedings of the 5th International Conference on Isotopes, Apr. 25-29, 2005, Brussels, Belgium, pp. 15-20.
Toporov, et al. "Reactor Production of High Specific Activity Tin-117m at RIAR", Proceedings of the 5th International Conference on Isotopes, Apr. 25-29, 2005, Brussels, Belgium, pp. 47-53.
Srivastava, "The Role of Electron-Emitting Radiopharmaceuticals in the Palliative Treatment of Metastatic Bone Pain and for Radiosynovestomy: Applications of Conversion Electron Emitter Tin-117m", Brazilian Archives of Biology and Technology, vol. 50, Sep. 2007, pp. 49-62.
Montgomery, et al., "Reactions of 116Cd With Intermediate Energy 3He and 4He Ions", Nuclear Physics A130, 1969, pp. 65-76.
Qaim, et al, "Production of Carrier-free 117mSn", Int. J. Appl. Radiat. Isot. vol. 35, No. 7, pp. 645-650, 1984.
Reebeles et al., "Alpha induced reaction on 114Cd and 116Cd: An experimental study of excitation functions" Nucl. Instr. And Meth. B, vol. 266, No. 21, Jun. 19, 2008, pp. 4731-4737.
European Patent Office, International Search Report and Written Opinion issued in related International application No. PCT/US2009/067467 dated Sep. 3, 2010.
Ermolaev, et al. "Production Yields of 117m-Sn from Natural Antimony Target in Proton Energy Range 145-35 MeV.", presented at the International Isotope Society Symposium, Edinburgh, UK, 2006, 2 pages.
Ermolaev, et al. "Production Yields of 117m-Sn from Natural Antimony Target in Proton Energy Range 145-35 MeV" Poster, presented at the International Isotope Society Symposium, Edinburgh, UK, 2006, 1 page.

* cited by examiner

*Primary Examiner* — Michael G Hartley
*Assistant Examiner* — Sean R Donohue
(74) *Attorney, Agent, or Firm* — Wood, Herron & Evans, LLP

(57) ABSTRACT

Compositions of high specific activity $^{117m}$Sn with specific activity of greater than 100 Ci/g Sn and methods of producing the same. The method includes exposing $^{116}$Cd to an α-particle beam of sufficient incident kinetic energy and duration to convert a portion of the $^{116}$Cd to $^{117m}$Sn to form an irradiated material. The irradiated material is dissolved to form an intermediate solution containing $^{117m}$Sn and $^{116}$Cd. The $^{117m}$Sn is separated from the $^{116}$Cd to yield high specific activity $^{117m}$Sn.

7 Claims, 1 Drawing Sheet

COMPOSITIONS OF HIGH SPECIFIC ACTIVITY SN-117M AND METHODS OF PREPARING THE SAME

BACKGROUND

The present invention relates to medically useful radioisotopes, and particularly to no-carrier-added (NCA) radioisotopes of tin and methods of preparing NCA radioisotopes of tin.

The use of beta particle-emitting radioisotopes for applications in nuclear medicine, oncology and interventional cardiology is rapidly increasing because of the availability of new pharmaceutical targeting approaches, which effectively concentrate or localize the radioactive vector at the target site with low uptake in non-target tissues. In this manner, the energy released from decay of the radioisotope can be localized for killing cells at the target site, such as the cells of a tumor. In this regard, the use of such radiopharmaceuticals has been shown to be effective in treating a variety of tumors and cancers.

Approximately 320,000 new cases of bone cancer are reported annually in the United States. A complex of $^{117m}$Sn ($Sn^{4+}$) chelated to dietheylenetriamine pentaacetic acid (DTPA) has been used in clinical trials as a bone seeking pain reliever for metastatic bone cancers which are currently untreatable and fatal. The $^{117m}$Sn complex does not sedate the patient, as do narcotic drugs, and provides selective radiation to the metastatic bone tumor while providing little radiation to the bone marrow. Consequently, the $^{117m}$Sn complex does not interfere with the bone marrow's ability to fight infection and does not interfere with blood clotting.

The nuclear-physical and biochemical properties of $^{117m}$Sn have enabled its useful application in nuclear medicine. The radioisotope $^{117m}$Sn possesses a relatively short 14-day half-life, a gamma emission of 158 keV (87%) and a high yield of short-range conversion electrons with energies of 126 keV (64%), 152 keV (26%) and 129 keV(11%).

The effectiveness of a radioisotope that emits particles, such as beta particles, can be improved if the specific activity of a radioisotope construct is increased and if a construct can be designed to specifically target a site of interest. However, specific activity is often limited by the available production methods for the isotope and the subsequent purification procedure. Therefore, a recognized need exists in the art for medically useful radionuclides with high specific activities that are targetable and have little or no effect on healthy tissue or organs.

A common method for the production of the radioisotope $^{117m}$Sn is through a "direct" method in a nuclear reactor via thermal neutron capture [$^{116}$Sn(n,γ) $^{117m}$Sn] or via non-elastic neutron scattering [$^{117}$Sn(n,n',γ) $^{117m}$Sn] reactions. Because the nonradioactive target atoms and radioactive product atoms are not chemically separable, the radioactive $^{117m}$Sn is diluted with significant amounts of the target isotope of tin. This excess of non-radioactive tin atoms therefore acts like a carrier, which inherently reduces the specific activity of the sample. With 97% or greater enriched-$^{117}$Sn as a target, maximum specific activities of up to about 20 to about 23 Ci/g have been achieved using thermal neutrons, [$^{117}$Sn (n, n'γ) $^{117m}$Sn]. This is substantially less than the theoretically possible specific activity of about 82,000 Ci/g, thereby leaving much room for improvement. In addition, the much longer-lived $^{113}$Sn isotope may be produced from the thermal neutron "direct" method with the naturally-occurring $^{112}$Sn isotopic impurity. The radioactive $^{113}$Sn isotope has a half-life of 115 days and two higher energy gamma rays of 392 keV (64%) and 255 keV (2%). The radioisotope $^{113}$Sn is generally considered harmful for nuclear medicine applications, because of the potential for extended patient exposure to radiation.

Conversely, there are several known methods of producing NCA $^{117m}$Sn. For example, reactions utilizing non-tin target atoms may employ proton-induced, $^3$He-particle-induced, or α-particle-induced reactions on cadmium and indium targets. Many reactions, such as $^{114}$Cd($^3$He, γ), $^{114}$Cd(α,n), $^{116}$Cd ($^3$He, 2n), $^{116}$Cd(α,3n), $^{115}$In(d, γ), $^{115}$In($^3$He, p), and $^{115}$In (α, pn), are known to lead to the formation of NCA $^{117m}$Sn, but are generally accompanied by production of some amount of the $^{113}$Sn radioisotope and other by-products.

Moreover, in addition to the manner of radioisotope generation, another major hindrance with producing NCA $^{117m}$Sn with high specific activity is the absence of an effective method for separating $^{117m}$Sn from the target material. Efficiently separating small quantities of a desired species from a much larger matrix, i.e. debulking, is notoriously difficult using conventional separation methods, such as chromatography or extraction. Historically, this very aspect of radionuclide purification provoked the use of a carrier, thereby rendering samples with reduced specific activity because of dilution by non-radioactive target atoms from the carrier.

Therefore, in view of the foregoing, a need exists for the production and isolation of NCA, high specific activity $^{117m}$Sn acceptable for use in radiopharmaceuticals.

BRIEF SUMMARY

In accordance with an embodiment of the invention, a composition of matter comprises $^{117m}$Sn having a specific activity of greater than 100 Ci/g Sn and a ratio of mass of Cd to mass of Sn less than 15,000:1.

In accordance with another embodiment of the invention, a product comprising high specific activity $^{117m}$Sn is prepared by a method that includes exposing isotopically-enriched $^{116}$Cd to a α-particle ion beam with an incident kinetic energy of about 30 MeV to about 60 MeV to convert a portion of the $^{116}$Cd target to $^{117m}$Sn to form an irradiated material. The irradiated material is dissolved to form an intermediate solution comprising $^{116}$Cd and $^{117m}$Sn. The $^{117m}$Sn is separated from the $^{116}$Cd via ion exchange chromatography by preparing an ion exchange resin column, loading the intermediate solution onto the ion exchange resin column, eluting the $^{117m}$Sn and the $^{116}$Cd from the ion exchange resin column with an eluent solution and collecting at least a portion of the eluent discharged from the ion exchange resin column.

In accordance with another embodiment of the invention, a product comprising high specific activity $^{117m}$Sn is prepared by a method that includes exposing isotopically-enriched $^{116}$Cd to a α-particle ion beam with an incident kinetic energy of about 30 MeV to about 60 MeV to convert a portion of the $^{116}$Cd target to $^{117m}$Sn to form an irradiated material. The irradiated material is dissolved to form an intermediate solution comprising $^{116}$Cd and $^{117m}$Sn. The $^{117m}$Sn is separated from the $^{116}$Cd via partitioning the intermediate solution between an organic solvent layer and an aqueous layer.

In accordance with another embodiment of the invention, a method of preparing a high-specific-activity $^{117m}$Sn composition includes exposing an isotopically-enriched $^{116}$Cd target to a α-particle ion beam with an incident kinetic energy of about 30 MeV to about 60 MeV to convert a portion of the $^{116}$Cd target to $^{117m}$Sn to form an irradiated material. The irradiated material is dissolved to form an intermediate solution comprising $^{116}$Cd and $^{117m}$Sn. The $^{117m}$Sn is separated from the $^{116}$Cd via ion exchange chromatography by preparing an ion exchange resin column, loading the intermediate solution onto the ion exchange resin column, eluting the $^{117m}$Sn and the $^{116}$Cd from the ion exchange resin column with an eluent solution and collecting at least a portion of the eluent discharged from the ion exchange resin column.

In accordance with another embodiment of the invention, a method of preparing a high-specific-activity $^{117m}$Sn composition includes exposing an isotopically-enriched $^{116}$Cd target to a α-particle ion beam with an energy of about 30 MeV to about 60 MeV to convert a portion of the $^{116}$Cd target to $^{117m}$Sn to form an irradiated material. The irradiated material is dissolved to form an intermediate solution comprising $^{116}$Cd and $^{117m}$Sn. The $^{117m}$Sn is separated from the $^{116}$Cd via partitioning the intermediate solution between an organic solvent layer and an aqueous layer to produce a product enriched in $^{117m}$Sn.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

The method and processes describe herein provide for the generation and isolation of NCA $^{117m}$Sn compositions at commercially viable yields and with high specific activities that have not been achieved by other methods known in the art. Briefly, the process includes preparing one or more targets comprising a thin-layer of enriched cadmium ($^{116}$Cd). The target comprising the enriched $^{116}$Cd is irradiated with a beam of α-particles to form $^{117m}$Sn. The irradiated cadmium layer is dissolved in a strong acid and the solution is subjected to a purification process to separate the desired $^{117m}$Sn from the matrix of the irradiated target.

Figure 1:
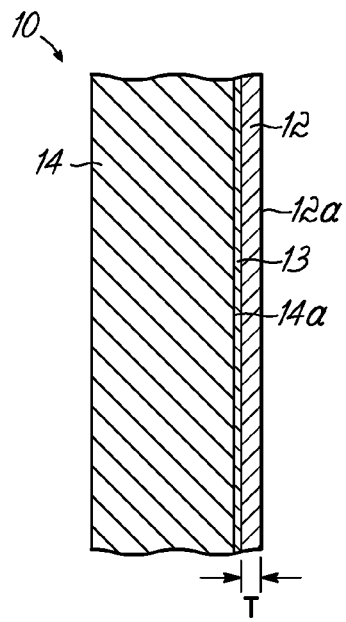
FIG. 1 is a cross-sectional view of a simplified target.

FIG. 1 depicts a cross-section of a target 10 comprising a thin-layer of a target material 12, an optional barrier layer 13, and a substrate 14. The composition of the target material 12 is selected to react with α-particles having energies ranging from 20 MeV to about 60 MeV to form radionuclides suitable for use in diagnostic or therapeutic radiopharmaceuticals. In one embodiment, isotopically-enriched cadmium is used for preparing NCA, high specific activity $^{117m}$Sn. In a specific embodiment, the isotopically-enriched isotope of cadmium is $^{116}$Cd, which can undergo the nuclear reaction $^{116}$Cd(α,3n) $^{117m}$Sn to produce NCA, high specific activity $^{117m}$Sn.

The target material 12 is preferably as chemically pure as commercially possible. The use of a target material that has a minimal amount of chemical impurities facilitates subsequent isolation and purification of the radionuclide of interest. To produce NCA $^{117m}$Sn characterized by a high specific activity, the target material should have a minimal amount of carrier (i.e., tin) impurities and/or other chemical impurities. These types of impurities may be difficult to chemically separate from the product. For example, the target material may be enriched $^{116}$Cd with greater than 99.9 wt % elemental purity and greater than 98 wt % isotopic purity.

The substrate 14, which supports the target material 12, is preferably composed of material that is chemically inert and separable from the target material 12 to allow for recovery and recycling of the target material 12. Additionally, the material from which barrier layer 13 and substrate 14 are comprised should be separable from the desired radionuclide produced during subsequent irradiation. The substrate 14 preferably has a melting point and a thermal conductivity that is at least about equal to the melting point and the thermal conductivity of the target material 12. One additional aspect to consider is for the barrier layer 13 and the substrate 14 to produce only a minimal amount of radioactive byproducts. Cadmium has a melting point (m.p.) of 321° C. and a thermal conductivity (k) of 97 W/mK. In one embodiment, the substrate is composed of copper, which has a melting point of 1085° C. and a thermal conductivity of 401 W/mK. In other embodiments, the substrate 14 can be composed of aluminum (m.p.=660° C., k=237 W/mK) or silver (m.p.=961° C., k=429 W/mK). Moreover, the configuration (e.g., shape, thickness, etc.) of the substrate 14 may exist in many geometrical configurations. Generally, the substrate 14 is shaped to facilitate use in a particular target holder and is preferably thick enough to provide adequate mechanical support to the target material 12 during irradiation.

Prior to forming a layer of target material 12 on the surface 14a of substrate 14, one or more additional layers, such as barrier layer 13, may be applied to the surface 14a. Barrier layer 13 may range from only a few microns to tens of microns in thickness. Useful attributes of barrier layer 13 may include serving as a protective layer to the underlying substrate 14 during the subsequent removal of the target material 12 by an etchant. This attribute inhibits leaching of the substrate 14 into the etchant when the target material 12 is removed. Additionally, barrier layer 13 may inhibit the absorption of target material and the produced $^{117m}$Sn into the surface 14a of substrate 14. This attribute prevents losses in activity. Therefore, exemplary materials for barrier layer 13 are preferably inert or kinetically-slow to react with strong acid etchants, such as hydrochloric acid. For example, barrier layer 13 may be prepared from suitable materials like nickel, rhodium or gold.

The barrier layer 13 and the layer of target material 12 can be formed on the surface 14a by a variety of methods, such as electroplating. Electroplating is achievable by any deposition technique known by those of ordinary skill in the art to achieve the desired areal density of the target material. For example, the areal density of enriched $^{116}$Cd to be electroplated ranges from about 50 mg/cm$^2$ to about 70 mg/cm$^2$. As another example, the areal density of enriched $^{116}$Cd electroplated is about 55 mg/cm$^2$.

Figure 2:
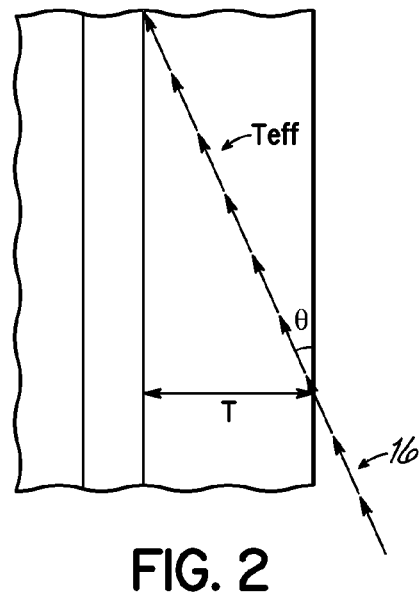
FIG. 2 is a cross-sectional view of the target layer as shown in FIG. 1.

The optimal thickness of the enriched $^{116}$Cd layer of target material 12 may vary depending on the specific target material used, the charged-particle beam energy and current, and the orientation of the target material 12 with respect to the beam during subsequent irradiation. In general, however, the thickness, T, of the layer of target material 12, as measured normal to the surface 12a of the target material 12, is preferably sufficient to result in a projected thickness, $T_{eff}$, which is sufficient to minimize the activation of the backing material 14. The optimization of the thickness may also take into account factors, such as cost per unit mass of the target material 12 and efficiency for heat transfer from the target material 12 to the substrate 14 during irradiation. As depicted in FIG. 2, the projected thickness, $T_{eff}$, refers to the thickness of the target layer measured in the direction of travel of the impinging ion beam 16 during irradiation. The projected thickness can be determined based on the normal thickness, t, and the angle θ at which the surface 12a of the target material 12 is oriented relative to the pathway of ion beam 16. Generally, for cyclotrons, the angle θ may vary between about 0.5° to about 2° for internally positioned targets and from about 5° to about 25° for externally positioned targets.

The optimal thickness of the target material layer can be determined by calculating a thickness T sufficient to reduce the α-particle beam kinetic energy to a desired level at the exit side of the target material 12. As stated above, excessive activation of the backing material 14, as well as any barrier layer, if present, is preferably minimized. For example, in one embodiment, the α-particle beam kinetic energy is reduced to about 20 MeV at the exit side of the target material 12. In view thereof, the effective thickness, $T_{eff}$, is about 300 μm to about 450 μm, which correspond to a thickness, T, of about 50 μm to about 80 μm for an incident α-particle ion beam angle θ equal to 10° and kinetic energy of 47.3 MeV. These ranges may vary based other factors, such as costs of material, heat transfer considerations and overall yield of the process.

The target 10, while being irradiated, is cooled by a cooling medium flow. The temperature and flow rate of the cooling medium are controlled to maintain the temperature of the exposed target layer surface 12a to less than about 200° C. For example, the temperature of the exposed target layer surface 12a is between 150° C. and 200° C. A flow sensor can be interlocked with the accelerator such that the accelerator shuts down if cooling medium flow is reduced to below a predetermined setpoint.

The target material 12 is irradiated with an accelerator beam of positive ions, in this instance α-particles, to form the radionuclide of interest. The particular accelerator design can include, for example, orbital accelerators such as cyclotrons, or linear accelerators.

Figure 3:
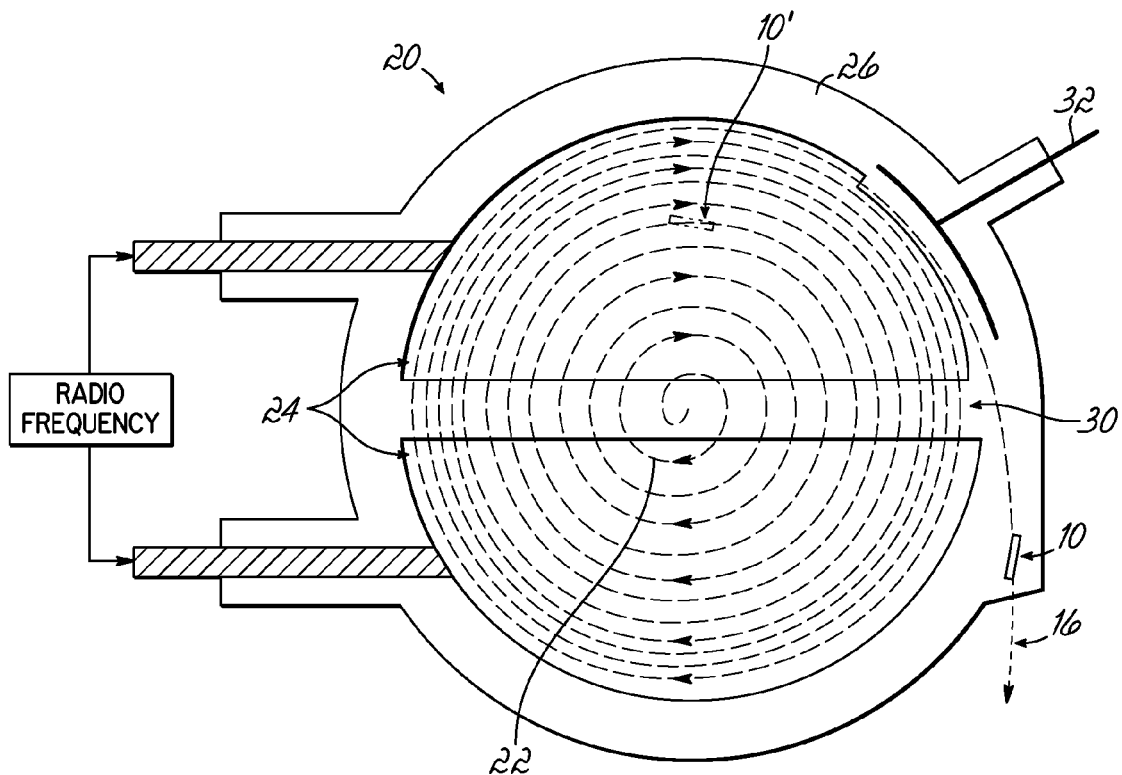
FIG. 3 is a diagrammatic view of a simplified cyclotron with internal and external target placements.

With reference to FIG. 3, irradiation of a target may be achieved using a cyclotron 20. The cyclotron 20 accelerates α-particles in a spiral path 22 inside two semicircular flat metallic cylinders or dees 24, which are placed in a flat vacuum chamber 26 to produce the ion beam 16. The two dees 24 are connected to a high frequency alternating voltage (not shown.) The dees 24 and the vacuum chamber 26 are placed between the two poles of a magnet (not shown) so that the magnetic field operates upon the α-particles that make up the ion beam 16 to constrain it to flat spiral paths 22 inside the dees 24. At the gap 30 between the dees 24, the α-particles experience an acceleration due to the potential difference between the dees 24. The ion beam 16 originates at the ion source at the center of the cyclotron 20, and as the ions spiral outward in the dees 24 they acquire a constant increase in energy for each passage across the gap between the dees 24. There can be two general locations for an internal beam target; the target can be place either before or after the deflector electrode 32. The target 10' can be located either inside the vacuum chamber 26 before the deflector electrode 32 or after extraction of the ion beam 16 from the spiral path 22 by a deflector electrode 32 into an evacuated chamber, as represented by target 10.

The ion beam 16 can be generated in a low or medium energy accelerator, which, as used herein, includes accelerators capable of generating an ion beam of α-particles having incident kinetic energies within a range of about 30 MeV to about 60 MeV and an ion beam current in a range of at least about 10 μA.

However, the accelerator need not be capable of generating an ion beam over the entire energy range and current range. The accelerator can be capable of generating ion beam energies in excess of 60 MeV, provided the accelerator is also capable of generating ion beams within the about 30 MeV to about 60 MeV range. The ion beam current useful for any specific embodiment of this invention is not limited to any specific amount. Instead, the ion beam current at a particular energy or energy range will generally be limited by accelerator capabilities and/or by heat-transfer considerations. Moreover, the ion beam current can be sufficient to produce an amount of radionuclide (as measured in curies) that is sufficient for clinical use in a radiopharmaceutical imaging or therapeutic agents or compositions.

The ion beam 16 may impinge the target 10 over an impingement area that substantially matches, but is slightly less than, the target layer surface area. Both the target layer surface area and the matching ion beam strike or impingement area are preferably as small as possible within heat transfer considerations. For example, the target layer surface area may be 7.5 cm×2.5 cm, 11 cm×2 cm, or 12.4 cm×1.6 cm.

The amount of time over which the target 10 is irradiated may be variable. Irradiation of the target nuclide at a particular ion beam current can generally be continued for a time sufficient to generate the desired quantities or amounts of radioactivity of the radionuclide of interest that are sufficient for use in preparing radiodiagnostic and radiotherapeutic agents or compositions suitable for clinical applications. The time required will vary depending on the nuclear reaction being effected, the ion beam energy and ion beam current. Typically, the irradiation time may vary between 4 to 24 hours.

In general, the specific activity of the $^{117m}$Sn composition at the end of bombardment significantly exceeds the near saturation point provided by the "direct" method, about 20 to about 23 Ci/g Sn, as described above. To be commercially viable, the α-particle bombardment of an enriched $^{116}$Cd target should provide for a specific activity of the $^{117m}$Sn composition of greater than 100 Ci/g Sn at the end of bombardment (EOB). In one example, the specific activity may be about 500 Ci/g to about 25,000 Ci/g Sn at EOB. As another example, the specific activity may be about 800 Ci/g to about 20,000 Ci/g Sn at EOB. As yet another example, the specific activity may be about 1,000 Ci/g to about 5,000 Ci/g Sn at EOB.

The very nature of radioactivity may affect the specific activity of the NCA $^{117m}$Sn product. After terminating the α-particle bombardment of the target layer 12, the production of $^{117m}$Sn from $^{116}$Cd ceases. Meanwhile, $^{117m}$Sn continuously decays with a half-life of 14.0 days to stable $^{117}$Sn. Thus, the radioactive decay affects the specific activity of the final isolated product. Moreover, delay time from EOB to processing, the time for performing a purification method, sample preparation, shipping time, etc. should all be considered in any determination of specific activity following EOB.

After irradiation, the target 10 is etched by a strong acid solution to dissolve the target layer 12, thereby separating the target layer 12 from the substrate 14 and producing an intermediate solution that contains $^{116}$Cd, $^{117m}$Sn, other radionuclides generated in the target matrix and other possible impurities, such as the nickel, iron, lead, the barrier layer material or the substrate material. This intermediate solution may be treated with other reagents, such as precipitating agents, oxidants, or ligands, such as chelating agents, to facilitate purification. Strong acids may include hydrochloric acid, nitric acid or hydrobromic acid, for example. Treatment reagents may include hydrogen peroxide, bromine water, bromates or peracids, for example. The target layer 12 may be dissolved in hydrochloric acid and treated with hydrogen peroxide. Alternatively, the intermediate solution may be evaporated to dryness or near dryness prior to purification.

For use as a pharmaceutical agent, the radionuclide must meet certain purity guidelines. As such, chemical purification of the intermediate solution comprising $^{117m}$Sn may be achieved via a variety of approaches to provide a product enriched in $^{117m}$Sn and diminished in cadmium and other impurities. Distillation, precipitation, extraction, or ion exchange column chromatography are all generally applicable methods for isolating a product enriched in $^{117m}$Sn with adequate pharmaceutical purity. A distillation purification may be achieved by utilizing the higher vapor pressure of $SnCl_4$ relative to the chlorides of cadmium and other elements present in the target matrix. Co-precipitation with other metals, such as iron, can be used to isolate tin. Liquid-liquid extractions may be performed using two immiscible solvents, such as hexones and aqueous solutions. Column chromatography may be effective using ion exchange resins as the stationary phase.

Ion exchange chromatography is suitable to achieve the desired purity of $^{117m}$Sn. The ion exchange resin used to form a separation column may be pretreated with an oxidant prior to use. For example, a mixture of an ion exchange resin, slurried in a suitable solvent, may be treated with an oxidant solution, thereby forming a pretreated resin. Pretreating the resin may inhibit the reducing activity of an ion exchange resin. For example, without this pretreatment, a $Sn^{4+}$ species in the sample may be reduced to a $Sn^{2+}$ species by the ion exchange resin, which then may become difficult to elute from the resin. From a thermodynamics perspective, the oxidant or oxidizing reagent must at least have a standard reduction potential which is more positive than 0.15 V, the reduction potential of $Sn^{4+}$ to $Sn^{2+}$. In one embodiment, bromate, which has a standard reduction potential of about 1.4 V, is used to pretreat the ion exchange resin.

In one example, AG1X4 resin, commercially available from Bio-Rad Laboratories, Hercules, Calif., is slurried in 9 N hydrochloric acid to form a mixture. While the resin slurry is stirred, solid $NaBrO_3$ is added to pretreat the resin. Afterwards, an ion exchange resin column may be prepared with the pretreated resin.

The dissolved target layer sample may be loaded onto the pretreated resin column and eluted with an appropriate mobile phase, such as 0.1 N $HNO_3$ or other dilute solutions of strong acids. Fractions of the eluted mobile phase may be collected, as is commonly performed by those skilled in the art. After elution, the fractions containing the product enriched in $^{117m}$Sn may be concentrated before utilizing the radioisotope for imaging or therapeutic purposes. Any fractions containing $^{117m}$Sn with insufficient purity, such as those contaminated with substrate material or target material, may be collected, concentrated and subjected to another purification process. The products enriched in NCA $^{117m}$Sn prepared according to embodiments of the invention have specific activities previously unattainable by the "direct" method and with purity levels suitable for medical uses, such as radiopharmaceutical or imaging compositions.

It should be noted, the specific activity of a product enriched in $^{117m}$Sn is a function of the specific activity existing at the end of bombardment, the time having elapsed since the end of bombardment, any introduction of cold tin to the sample during processing and combinations thereof. Therefore, in view of the nature of radioactive decay, it is advantageous to limit the time between the end of bombardment and actual use. If a sample possessing a specific activity of a certain range is desirable, then time delay after bombardment, processing time and shipping time must be considered.

The high specific activity NCA $^{117m}$Sn product prepared according to the embodiments of the invention may be useful for therapeutic or diagnostic purposes. Radiopharmaceutical compositions may be prepared using the high specific activity NCA $^{117m}$Sn product in combination with ligands, such as chelators or targeting molecules. For example, 1,4,7,10-tetraazacyclododecane-1,4,7,10-tetraacetic acid (DOTA) or diethylene triamine pentaacetic acid (DTPA) may be used to form radiopharmaceutical compositions with high specific activity NCA $^{117m}$Sn.

As used herein, a ligand may be an atom, ion, or molecule that bonds to a central metal, and generally involves the formal donation of one or more of its electrons. The metal-ligand bonding may range from covalent to more ionic. Furthermore, the metal-ligand bond order can range from one to three. Chelators are bi- or multidentate ligands and are often organic compounds. A chelator forms a chelate complex with a metal through a process known as complexation, in which the metal ion is bound to two or more atoms of the chelating agent. A targeting molecule is a type of ligand that demonstrates an affinity or selectivity toward a desired biological target. Biological targets may include specific cell types, receptors, antigens, and the like. Exemplary targeting molecules include other types of ligands, such as proteins, antibodies, etc. In some instances, a pharmaceutical ligand may be complex structure derived from the combination of two or more species of ligands, such as an antibody covalently bonded to a chelator.

The metallic burden is an additional aspect that should be considered when the high specific activity NCA $^{117m}$Sn product, prepared according to the embodiments of the present invention, is to be used for preparing a radiopharmaceutical composition. Excessive levels of metallic impurities, such as cadmium, may compete with, interfere with or inhibit the desired binding of a ligand to the $^{117m}$Sn. In addition, it should be appreciated that the level of metallic impurities may vary depending on the chosen purification method. In one embodiment, the product enriched in NCA $^{117m}$Sn has a cadmium concentration less than 5,000 mg/L and a ratio of the mass of Cd to the mass of Sn less than 15,000:1. In another embodiment, the product enriched in NCA $^{117m}$Sn has a cadmium concentration less than 1,000 mg/L and a ratio of the mass of Cd to the mass of Sn less than 1,000:1. In yet another embodiment, the product enriched in NCA $^{117m}$Sn has a cadmium concentration less than 50 mg/L and a ratio of the mass of Cd to the mass of Sn less than 100:1.

It is convenient to measure a metallic impurity level relative to the amount of $^{117m}$Sn, measured in millicuries (mCi), in the high specific activity NCA $^{117m}$Sn product. The metallic impurities may include, but are not limited to cadmium, iron, copper, lead, nickel and zinc. For example, one sample of high specific activity NCA $^{117m}$Sn product suitable for use in a radiopharmaceutical composition, prepared according to the embodiments of the present invention, had a cadmium content less than 20 µg/mCi, an iron content less than 2 µg/mCi and each other metal present in the sample was less than 3 µg/mCi, per species.

One suitable radiopharmaceutical composition, $^{117m}$Sn ($Sn^{4+}$) DTPA (diethylene triamine pentaacetic acid), which is useful for the treatment of bone tumors and pain associated with bone cancer, may be prepared using the high specific activity NCA $^{117m}$Sn product as disclosed herein. After the ion exchange column chromatography purification, the fractions containing the product enriched in $^{117m}$Sn may be concentrated to dryness and the residue dissolved in a minimal amount of concentrated hydrochloric acid to form a solution of $^{117m}SnCl_4$. A reducing agent may be added, such as cold metallic tin, to reduce the $Sn^{4+}$ to the $Sn^{2+}$ oxidation state, thus forming a solution of $^{117m}SnCl_2$. Solid DTPA may be added to this solution of $^{117m}SnCl_2$ in a molar amount of about 1 to about 3, DTPA to $^{117m}SnCl_2$. For example, the molar amount of DTPA to $^{117m}SnCl_2$ may be about 1 to about 1.2. After permitting the DTPA to react with $^{117m}SnCl_2$ to form $^{117m}Sn\ (Sn^{2+})$ DTPA, the solution may be oxidize from $^{117m}Sn\ (Sn^{2+})$ DTPA to $^{117m}Sn\ (Sn^{4+})$ DTPA, either by exposure to air or by treatment with an oxidizing agent, such as hydrogen peroxide, for example. The $^{117m}Sn\ (Sn^{4+})$ DTPA complex may be isolated as a solid.

The $^{117m}Sn\ (Sn^{4+})$ DTPA complex solid may be dissolved in water and optionally heated, for example in a boiling water bath, to facilitate further complexation. The temperature should be sufficient to facilitate complexation, without destroying the desired product. Examples of such temperature ranges are as achieved in a boiling water bath preferably between about 90° C. to about 100° C. If a heating step is performed, the $^{117m}Sn\ (Sn^{4+})$ DTPA solution may be cooled to approximately room temperature prior to use. The pH of the solution containing $^{117m}Sn\ (Sn^{4+})$ DTPA may be adjusted to between about 3 to about 5, preferably between about 4 to about 4.5. The solution may be reheated and cooled.

The resulting pharmaceutical composition $^{117m}Sn\ (Sn^{4+})$ DTPA may have a molar ratio of DTPA to $^{117m}Sn\ (Sn^{4+})$ of between about 3 to about 1. That is, in the pharmaceutical composition, for each mole of $^{117m}Sn\ (Sn^{4+})$ (or total tin) there will be from about one to about three moles of DTPA, either chelated to $^{117m}Sn\ (Sn^{4+})$ or in unchelated form. For example, the resulting pharmaceutical composition $^{117m}Sn\ (Sn^{4+})$ DTPA may contain from about one to about 1.2 moles of DTPA for each mole of $^{117m}Sn\ (Sn^{4+})$.

The pharmaceutical composition $^{117m}Sn\ (Sn^{4+})$ DTPA may optionally include the addition of an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition may also include the addition of stabilizers, preservatives, buffers, or other additives known to those of skill in the art.

The following descriptions serve to provide exemplary embodiments of the invention. Unless specified otherwise, all reagents are high purity, analytical grade or HPLC grade reagents that are available from commercial sources. The highly enriched $^{116}Cd$, (>99.9 wt % cadmium, >98.4 isotopic % cadmium-116) was purchased from Trace Sciences International Inc. Wilmington, Del. The specific activity (Ci/g) of the cyclotron produced NCA $^{117m}Sn$ was determined by high purity Ge detector. The chemical purity, including the content of other metals, was determined by inductively-coupled plasma (ICP) analysis on a Varian VistaPro ICP-OES.

EXAMPLE 1

TARGET PREPARATION—A solution of highly enriched $^{116}Cd$ was prepared by dissolving 2 grams of the highly enriched $^{116}Cd$ in 60 mL of 0.6 N sulfuric acid. The solution was placed in a plating cell, in contact with a clean copper target. A power supply was connected to the target solution and the solution electrode such that the negative terminal was attached to the target and the positive terminal was attached to the solution electrode. The current was set to a range of about 60 mA to about 100 mA and the target was plated over a period of about 3 hours. Periodically, the process was halted to determine the mass of $^{116}Cd$ plated on the target until a mass of about 1.1 g to about 1.2 g was achieved. The $^{116}Cd$-electroplated target was stored in a dessicator under vacuum until use.

NCA $^{117m}Sn$ PRODUCTION—Irradiation was performed with 47.3 MeV α-particles on the MC50 cyclotron at the University of Washington Medical Center in Seattle, Wash. Initially low beam currents were used for to evaluate the activity, specific activity and by-product mixture. After bombardment, the irradiated target was allowed to rest to allow short-lived products to decay away, then the sample was measured with a high-purity Ge detector to determine activity. At this point, $^{117m}Sn$ is the overwhelmingly dominant radioactive product. The only significant other radioactive products in the irradiated cadmium target material were $^{115}Cd$, $^{111}In$ and to a lesser extent, $^{115m}Cd$. The $^{113}Sn$ and other by-products were at the limit of detection, being below 0.1%.

Subsequently, longer (up to 12 hrs) irradiations were made with increasing beam currents up to 91 µA without any substantial loss of target material. Yields were found to be linear with integrated beam, typically in the region of 170 µCi/µA h. A typical 10-hr irradiation at 70 µA yielded about 120 mCi. The specific activity range was typically between about 1000 to about 5000 Ci/g at end of bombardment (EOB) although values as high as about 23,000 Ci/g (EOB) were measured in the final radiochemical product. Varying specific activity numbers can result from even trace quantities of environmental tin being inadvertently introduced during the chemical processing.

SEPARATION BY ION EXCHANGE CHROMATOGRAPHY—After irradiation, the $^{117m}Sn$ was separated from the target material and other contaminants using an ion exchange resin column. A 1.1 gram irradiated cadmium target layer was removed from the copper backing material by dissolving in approximately 100 mL of 4 N hydrochloric acid heated to 60° C. The target layer was dissolved over a 1.5 hour etching period. Care was taken to minimize exposing the copper backing material to the acid solution. The resulting solution was then evaporated to near dryness at 60° C. using blower-assisted evaporation. Concentrated $HNO_3$ was introduced throughout the evaporation to ensure conversion of all the tin species to the +4 oxidation state. The residue was dissolved in 20 mL of concentrated $HNO_3$ and 5 mL of 30% $H_2O_2$, followed by evaporation to near dryness and redissolving in a minimum of 9 N HCl. The resulting solution was then loaded onto an ion exchange resin column comprising AG1X4 resin (column size=3 cm×50 cm column; 160 grams of BioRad AG1-X4 resin slurried in 100 mL of 9 N HCl to which was added 16 grams of solid $NaBrO_3$) pretreated with 250 mL of 9 N HCl under a gravity flow rate. The elution order of the major constituents was copper, tin, and cadmium, respectively. The fraction containing copper was eluted in the first 150 mL to 200 mL of 0.1 N $HNO_3$ passed through the column. When $^{117m}Sn$ activity was detected, the fractions containing tin were collected over a 500 mL to 600 mL elution to recover approximately 80% of the $^{117m}Sn$ activity. The remaining 20% of $^{117m}Sn$ activity was eluted in 400 mL of 0.1 N $HNO_3$, accompanied by cadmium break-through. This $^{117m}Sn$—cadmium fraction may be subjected to a second ion exchange column purification to maximize isolation of $^{117m}Sn$. The $^{117m}Sn$—containing fractions were concentrated to near dryness under dryer assisted evaporation, while an HCl replacement was performed with 80 mL of 8 N HCl to ensure conversion of $^{117m}Sn^{4+}$ to the $^{117m}SnCl_4$ species. The resulting residue was redissolved in about 1 mL of 1 N HCl to provide a product enriched in $^{117m}Sn$ as a 1.0 mL sample containing 31.3 mCi $^{117m}Sn$ having a specific activity of 10,200 Ci/g Sn with 0.1% by activity $^{113}$Sn. This product enriched in NCA $^{117m}$Sn had a cadmium concentration of about 1 mg/L and had a mass ratio of Cd-to-Sn of less than 1:1.

SEPARATION BY LIQUID-LIQUID EXTRACTION— After irradiation, the $^{117m}$Sn was separated from the target material and other contaminants by liquid-liquid extraction. A 1.1 gram irradiated cadmium target layer was removed from the copper backing material by dissolving in approximately 100 mL of 4 N hydrochloric acid heated to 60° C. The target layer was dissolved over a 1.5 hour etching period. Care was taken to minimize exposing the copper backing material to the acid solution. The resulting solution was extracted by mixing with 3×20 mL of hexone (4-methyl-pentan-2-one) that had been pre-equilibrated with 2 N HCl. The organic layers containing the bulk of the $^{117m}$Sn were combined and then back-extracted with 3×20 mL 0.05 N HCl. The aqueous back-extraction layers were combined together, evaporated to near dryness under dryer assisted evaporation and the resulting residue was redissolved in about 40 mL of 2 N HCl and the hexone extraction procedure was repeated. The combined back-extraction layers were evaporated to near dryness under dryer assisted evaporation and resulting residue was redissolved in about 2 mL of 6 N HCl to provide a 2.1 mL sample containing 14.3 mCi $^{117m}$Sn having a specific activity of 15,580 Ci/g Sn with less than 0.1% by activity $^{113}$Sn. This product enriched in NCA $^{117m}$Sn had a cadmium concentration less than 570 mg/L and had a mass ratio of Cd-to-Sn of about 1,300.

While various embodiments of the invention have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method of preparing a high-specific-activity $^{117m}$Sn composition, the method comprising:

exposing a target layer enriched in $^{116}$Cd to an α-particle ion beam with an incident kinetic energy of about 30 MeV to about 60 MeV to convert a portion of the $^{116}$Cd in the target layer to $^{117m}$Sn;

dissolving the target layer to form an intermediate solution containing the $^{117m}$Sn and the $^{116}$Cd;

preparing an ion exchange resin column;

loading the intermediate solution onto the ion exchange resin column;

eluting the $^{117m}$Sn and the $^{116}$Cd from the ion exchange resin column with an eluent solution to separate at least a portion of the $^{117m}$Sn from at least a portion of the $^{116}$Cd; and collecting at least a portion of the eluent solution discharged from the ion exchange resin column to provide a product enriched in the $^{117m}$Sn, wherein the $^{117m}$Sn in the product has a specific activity of greater than 100 Ci/g, and wherein the ion exchange resin is pretreated with an oxidant prior to loading the intermediate solution onto the ion exchange resin column.

2. The method of claim 1 wherein preparing the ion exchange resin column further comprises:

pre-treating an ion exchange resin with an oxidant to form a pretreated ion exchange resin; and preparing the ion exchange resin column with the pretreated ion exchange resin.

3. The method of claim 2 wherein the oxidant comprises a salt of bromate.

4. The method of claim 2 wherein the oxidant comprises sodium bromate.

5. The method of claim 1 wherein a mass ratio of all Cd isotopes in the product to all Sn isotopes in the product is less than 15,000:1.

6. The method of claim 1 wherein the $^{117m}$Sn in the product has a specific activity ranging from about 500 Ci/g to about 25,000 Ci/g.

7. The method of claim 1 wherein the $^{117m}$Sn in the product has a specific activity ranging from about 1,000 Ci/g to about 5,000 Ci/g.

* * * * *